US006699665B1

(12) United States Patent
Kim et al.

(10) Patent No.: US 6,699,665 B1
(45) Date of Patent: Mar. 2, 2004

(54) MULTIPLE ARRAY SYSTEM FOR INTEGRATING BIOARRAYS

(75) Inventors: Enoch Kim, Boston, MA (US); David Duffy, Cambridge, MA (US)

(73) Assignee: Surface Logix, Inc., Brighton, MA (US)

( * ) Notice: Subject to any disclaimer, the term of this patent is extended or adjusted under 35 U.S.C. 154(b) by 466 days.

(21) Appl. No.: 09/709,776

(22) Filed: Nov. 8, 2000

(51) Int. Cl.[7] ................................ C12Q 1/68
(52) U.S. Cl. ................ 435/6; 435/91.1; 435/396; 435/288.4; 435/DIG. 49; 530/334; 536/25.3
(58) Field of Search .................. 435/395, 396, 435/401, 288.4, 288.5, 305.2, 6, 91.1, DIG. 49; 530/334; 536/25.3

(56) References Cited

U.S. PATENT DOCUMENTS

| | | | |
|---|---|---|---|
| 4,240,751 A | 12/1980 | Linnecke et al. | 356/409 |
| 4,728,591 A | 3/1988 | Clark et al. | 430/5 |
| 4,802,951 A | 2/1989 | Clark et al. | |
| 4,842,633 A | 6/1989 | Kuribayashi et al. | 65/44 |
| 4,999,489 A | 3/1991 | Huggins | 250/226 |
| 5,079,600 A | 1/1992 | Schnur et al. | 357/4 |
| 5,143,854 A | 9/1992 | Pirrung et al. | 436/518 |
| 5,202,227 A | 4/1993 | Matsuda et al. | 430/320 |
| 5,324,591 A | 6/1994 | Georger, Jr. et al. | 428/552 |
| 5,510,481 A | 4/1996 | Bednarski et al. | 536/120 |
| 5,512,131 A | 4/1996 | Kumar et al. | |
| 5,599,695 A | 2/1997 | Pease et al. | |
| 5,679,310 A | 10/1997 | Manns | 422/102 |
| 5,691,018 A | 11/1997 | Kelley et al. | 428/36.8 |
| 5,719,060 A | 2/1998 | Hutchens et al. | 436/174 |
| 5,776,748 A | 7/1998 | Singhvi et al. | 435/180 |
| 5,856,082 A | 1/1999 | Aebersold et al. | 435/4 |
| 5,894,063 A | 4/1999 | Hutchens et al. | 436/155 |
| 5,900,160 A | 5/1999 | Whitesides et al. | 216/41 |
| 5,942,443 A | 8/1999 | Parce et al. | 436/514 |
| 5,976,826 A | 11/1999 | Singhvi et al. | 435/29 |
| 6,001,556 A | 12/1999 | Charych et al. | 435/5 |
| 6,020,208 A | 2/2000 | Hutchens et al. | 436/174 |
| 6,027,942 A | 2/2000 | Hutchens et al. | 436/173 |
| 6,071,610 A | 6/2000 | Jarrell et al. | 428/335 |
| 6,096,510 A | 8/2000 | Hochman | 435/29 |
| 6,558,904 B2 | 5/2003 | Ermantraut et al. | 435/6 |

FOREIGN PATENT DOCUMENTS

WO   WO 98/36827   8/1998

OTHER PUBLICATIONS

George B. Sigal et al., "Using Surface Plasmon Resonance Spectroscopy To Measure the Association of Detergents with Self–Assembled Monolayers of Hexadecanethiolate on Gold", Langmuir, 1997, 13, pp. 2749–2755.

John E. Hale, "Irreversible, Oriented Immobiliazation of Antibodies to Cobalt–Iminodiacetate Resin for Use as Immunoaffinity Media", Analytical Biochemistry, 1995, 231, 46–49.

(List continued on next page.)

*Primary Examiner*—David A. Redding
(74) *Attorney, Agent, or Firm*—Kenyon & Kenyon

(57) ABSTRACT

A multiple level micro-array system for integrating micro-arrays of biomolecules, including biological, chemical and biochemical elements. The multiple level micro-arrays are formed using soft lithography techniques and elastomeric membranes to shield or pattern various portions of a suitable substrate with biomolecules. Additional levels are formed using membranes with various through holes which either isolate, stratify or shield the patterned biomolecules from subsequent patterning or addition of an assay solution.

45 Claims, 12 Drawing Sheets

OTHER PUBLICATIONS

George B. Sigal et al., "A Self-Assembled Monolayer for the Binding and Study of Histidine-Tagged Proteins by Surface Plasmon Resonance", Anal. Chem., 1996, 68, 490–497.

Rebecca J. Jackman et al., "Using Elastomeric Membranes as Dry Resists and for Dry Lift-Off", Langmuir, 1999, vol. 15, pp. 2973–2984.

Albert Folch and Mehmet Toner, "Cellular Micropatterns on Biocompatible Materials", Biotechol. Prog., 1998, vol. 14 No. 3, pp. 388–392.

Younan Xia and George M. Whitesides, "Soft Lithography", Angew. Chem. Ins. Ed., 1998, vol. 37, pp. 551–575.

David C. Duffy et al., "Patterning Electroluminscent Materials with Feature Sizes as Small as 5 μm Using Elastomeric Membranes as Masks for Dry Lift-Off", Advanced Materials, vol. 11 No. 7, pp. 546 552.

M. Saleemuddin, "Bioaffinity Based Immobilization of Enzymes", Advances in Biochemical Engineering/Biotechnology, 1999, vol. 64, pp. 204–226.

D.W. Branch et al., "Microstamp patterns of biomolecules for high-resolution neuronal networks", Medical & Biological Engineering & Computing, 1998, vol. 36, pp. 135–141.

Jesus E Gonzalez and Paul Negulescu, "Intracellular detection assays for high-throughout screening", Current Opinion in Biotechnology, 1998, 9:624–631.

Lora Mere et al, "Miniaturized FRET assays and microfluidics: key components for ultra-high throughput screening", DDT, Aug. 8, 1999, vol. 4 363–369.

G. Sitta Sittampalam et al., "High-throughput screening: advances in assay technologies", Current Opinion in Chemical Biology, 1997, 1:384–391.

Rebecca J. Jackman et al., "Fabricating Large Arrays of Microwells with Arbitrary Dimensions and Filling Them Using Discontinuous Dewetting", Anal. Chem., 1998, 2280–2287.

Andre Bernard et al., "Printing Patterns of Proteins", Langmuir, Apr. 28, 1998, No. 14, No. 9, pp. 2226–2228.

Hannes Kind et al., "Patterned Electroless Deposition of Copper by Microcontact Printing Palladium (II) Complexes on Titanium-Covered Surfaces", Langmuir, Aug. 8, 2000, vol. 16, N. 16, pp. 6367–6373.

PEEL AWAY CURVED LAYER OF PDMS INVERT LAYER AND SEAL ON TO GOLD SURFACE

PATTERNED SUBSTRATE AND ONE PDMS MEMBRANE

+

PATTERNED SUBSTRATE PDMS MEMBRANE

↓ PLACE MEMBRANE ON TOP OF THE SUBSTRATE

↓ CARRY OUT DIFFERENT ASSAYS IN EACH AREA DEFINED BY MEMBRANE

MULTIPLE ARRAY SYSTEM FOR INTEGRATING BIOARRAYS

FIELD OF THE INVENTION

The present invention relates to multiple array systems for integrating arrays of biomolecules, including biological, chemical and biochemical elements.

BACKGROUND OF THE INVENTION

There is a need to rapidly assay compounds for their effects on various biological processes. Nearly all biological activity is regulated by the interactions of proteins in cells. Proteins are the catalysts, motion transducers, and signal mediators of cells. They control cell division, cell growth, cell differentiation, cell death, and mediate the responses of cells to their environments. Enzymologists have long sought better substrates, better inhibitors and better catalysts for enzymatic reactions. To understand cellular processes, we therefore need to monitor the activity of proteins, and to determine the networks of interactions of proteins within cells.

In the past, tools available to biologists only allowed the study of one interaction at a time because there were no analytical tools that would allow large numbers of protein interactions to be monitored simultaneously. Thus, a system that would allow parallel analyses of protein interactions would be of immense value and would speed the progress of biological discovery.

In addition, there is a need to rapidly assay or screen compounds for potential drug candidates. Drug discovery is a long, multiple step process involving the identification of specific disease targets, development of assays based on a specific target, validation of the assays, and optimization and automation of the assay to achieve screening of a large number of candidates. After high throughput screening of compound libraries using various assays, hit validation and hit compound optimization procedures are employed. Performing a screen on many thousands of compounds thus requires parallel processing of many compounds and assay component reagents. In addition, to find lead compounds for drug discovery programs, large numbers of compounds are often screened for their activity as enzyme inhibitors or receptor agonists/antagonists. Large libraries of compounds are needed for such screening. As a result of developments in this field, it is now possible to simultaneously produce combinatorial libraries containing hundreds of thousands of small molecules for screening. With such libraries on hand there is an ever increasing need to rapidly screen the thousands of these new potential drug candidates.

One common approach to drug discovery involves presenting macromolecules implicated in causing a disease (disease targets) in bioassays in which potential drug candidates are tested for therapeutic activity. Such molecules could be receptors, enzymes, transcription factors, co-factors, DNA, RNA, growth promoters, cell-death inducers, or non-enzymatic proteins and peptides. Another approach involves presenting whole cells or organisms that are representative of the causative agent of the disease. Such agents include bacteria and tumor cell lines. Thus, there is a need to be able to screen the effects of various drug candidates on assorted cells and cell lines.

The conventional methods for assessing the effects of various agents or physiological activities on biological materials utilize standard microtiter plates. See for example, U.S. Pat. No. 6,083,763. Unfortunately microtiter plates do not allow for expansion into multiple parameter assays. For example, assessment of the effect of a physiological agent, such as a drug, on a population of cells or tissue grown in culture conventionally provides information relating to the effect of the agent on the cell or tissue population only at specified points in time. In addition, current assessment techniques generally only provide information relating to a single or a small number of parameters. For example, candidate agents are systematically tested for cytotoxicity, which may be determined as a function of concentration. A population of cells is treated, and at one or several time points following treatment, cell survival is measured. Thus, cytotoxicity assays generally do not provide any information relating to the cause(s) or time course of cell death but merely show whether cells die or survive. To elucidate the mechanism of the interaction/activity of agents, an assay capable of simultaneously monitoring several parameters is required.

In addition, therapeutic agents are frequently evaluated based on their physiological effects on a particular metabolic function. An agent is administered to a population of cells or a tissue sample, and the metabolic function of interest is assayed to assess the effect of the agent. This type of assay provides useful information, but it does not provide information relating to the mechanism of action, the effect on other metabolic functions, the time course of the physiological effect, general cell or tissue health, and the like.

Despite the great value that screening libraries of molecules has for identifying useful pharmaceutical compounds and improving the properties of a lead compound, the difficulties of screening, and especially the lack of "functional" screening methods, of these libraries has limited the impact that these methods have had in drug discovery and development. Thus, there remains a need for an assay system that allows a simultaneous screen for multiple target-ligand interactions in drug discovery and in the development of lead compounds. There exists a strong need for a high throughput multilevel assay system to test potential drug candidates and to obtain biologically and clinically relevant information. This need is not limited to drug discovery but also concerns diagnostic and clinical diagnosis arenas as well.

The relationship between structure and function of molecules is a fundamental issue in the study of biological systems. Structure-function relationships are important for understanding biological phenomena such as enzyme function, cellular communication, and cellular control and feedback mechanisms to name a few. Understanding how various molecules interact with each other, such as protein-receptor interactions for example, often provides the first step in understanding biomolecule function.

Modern pharmaceutical drug discovery often relies on the study of structure-function relationships. Much contemporary drug discovery involves discovering novel ligands with desirable patterns of specificity for biologically important receptors. Thus, the length of time necessary to bring new drugs to market could be greatly reduced by assay systems that allow rapid screening of structure-function relationships of large numbers of ligands.

Within the general drug discovery strategies, several sub-strategies have been developed. One spatially-addressable strategy that has emerged involves the generation of peptide libraries on immobilized pins that fit the dimensions of a standard 96 well micro-titer plate. See PCT Patent Publication Nos. 91/17271 and 91/19818, each of which is incorporated herein by reference. This method has been used to identify peptides that mimic discontinuous epitopes as described in Geysen et al., "Screening Chemically Synthesized Peptide Libraries for Biologically Relevant Molecules," Bioorg Med Chem. Lett. 3: 397–404 (1993), and to generate benzodiazepine libraries as described in U.S. Pat. No. 5,288,514 and Bunin et al., "The Combinatorial Synthesis and Chemical and Biological Evaluation of a 1,4-Benzodiazepine Library," Proc. Natl. Acad Sci. 91:4708–4712 (1994). The structures of the individual library members can be determined from the pin location in the micro titer plate and the sequence of reaction steps (called a "synthesis histogram") performed during the synthesis.

In addition to the above-mentioned methods used in drug discovery, several trends are fueling interest in the application of cell-based assays for drug discovery. Cell-based screens offer the potential to shorten the time between target validation and lead drug discovery because these assays can be miniaturized to increase screening throughput and reduce costs. Information about target biology is encouraging development of assays for specific, often subtle effects on target function. For example, cell based assays have been used to screen for modulators of ion channel kinetics, allosteric regulators of receptor agonist efficacy and protein interactions. Unfortunately, these assays are often difficult to format using traditional ligand displacement or biochemical methods because the binding sites of modulators may be unknown.

Advances in biology, chemistry and instrumentation have provided user-friendly tools for the development of optical indicators of cell function. Many of these tools allow direct detection of target function in living cells. Most of these tools employ either fluorescent or luminescent reporter molecules and allow cell-based assays for most targets, including receptors, ion channels and intracellular enzymes. Examples of these tools include adsorbance assays, fluorescence intensity assays, fluorescence resonance energy transfer ("FRET") assays, fluorescence distribution assays, fluorescence polarization, and luminescence assays. These novel optical assays promise to accelerate the use of living cells in screens for drug discovery.

Common therapeutic targets for high throughput screening ("HTS") are enzymes, cell surface receptors, nuclear receptors, ion channels, signal transduction proteins, cell surface glycoproteins and proteoglycans. Compounds that interact with these targets are usually identified using in vitro biochemical assays.

Cell-based assays using engineered mammalian cell lines provide the most biologically relevant information because the ligand interaction occurs in the biological environment of the target. This provides opportunities to simultaneously monitor secondary cellular events. Thus, because of the numerous novel cell-based assays that are currently available there is a need for a multiple level array system that can be used in conjunction with these cell-based assays. The present invention addresses this need and specifically provides for high density arrays that can be used in cell based assays.

These assays and other conventional assays, as well as HTS, such as DNA analysis, gene expression profiling, mapping for single nucleotide polymorphisms (SNP's), and enzyme linked immunosorbent assay (ELISA) and others rely on arraying of biomolecules.

In a recent development, the techniques of photolithography, chemistry and biology have been combined to array large collections of biocompounds on the surface of a substrate. See U.S. Pat. No. 5,143,854 and PCT patent publication Nos. 90/15070 and 92/10092, each of which is incorporated herein by reference.

"Genechip" technology as well as photolithography to generate patterns of target oligonucleotides (See U.S. Pat. No. 5,599,695) have revolutionized the ways assays are performed. Robotic spotting systems have been developed to "print" arrays of nucleic acids and other materials on surfaces for assay development. Unfortunately, both photolithography and robotic array systems require expensive equipment. In addition, processing conditions required in photolithography are often incompatible with many biochemical and biological materials. Robotic spotting systems work well when used with homogeneous fluids, but they do not work efficiently when attempting to pattern cells directly. Although, silkscreen printing and ink-jet printing have recently shown much promise in the generation of biological arrays, they suffer from their inability to generate patterns having fine resolutions. Obtaining sub-100 $\mu$m resolution is difficult with these techniques.

Despite these difficulties, protein arrays provide a promising tool that allows biological researchers to perform high throughput assays. Various concepts have been proposed for protein arrays. The most common is composed of arrays of monoclonal antibodies that bind to specific proteins in a way similar to the way that arrays of cDNA capture mRNA. See Arenkov, P., et al., Analytical Biochemsitry, 2000, 278, pp. 128–131. Other approaches include the use of arrays of chemicals which bind proteins. Arrays such as these have been used to isolate proteins, but no array system useful for monitoring interactions between proteins yet exists.

Thus, there is a need for a multilevel array system that can utilize and take advantage of the recent advances involving cell-based assays, lithography, and protein arrays. There is a need for a multiple parameter assay which can perform repeated, accurate assay screens at a very small volume. A new system in which multiple targets and ligands can be identified as new pharmacological, diagnostic, experimental, or other useful agents would fill this need as well as an assay system that has arrays upon arrays to allow for rapid screening of multiple targets, such as cells or proteins, against multiple agents, such as drug-candidate compounds. The present invention provides a multilevel array assay system that can be used in conjunction with standard microtiter plates, such as 6-well, 12-well, 24-well, 96-well, 384-well, or 1536-well microtiter plates, microtiter plate readers and microtiter plate robotic systems. The present invention provides a novel multilevel array system that can be used in HTS, in the study of protein-protein interaction, cell based assays, and other known biological assays. In addition, the present invention provides a multiple array that allows for micro patterning of cells using soft lithography methods, i.e. patterning of cells in an area of about 100 microns in diameter.

SUMMARY OF THE INVENTION

The present invention provides multiple level micro arrays as well as a method of preparing the arrays. The arrays can be composed of proteins, nucleic acids, cells, antibodies, enzymes, glycoproteins, proteoglycans, and other biological materials, as well as chemical or biochemical substances. The invention is especially useful in drug discovery and clinical diagnostic applications. Bioarrays can provide large amounts of data about biological systems, such as their disease state or the effect of a drug. These arrays can be integrated into high throughput screening methods that are commonly used in drug discovery, for example, robotic systems. Additionally, the arrays can be designed to take advantage of systems developed for current assay formats, such as detection systems and robotic systems and the like which are designed to handle 6-well, 12-well, 24-well, 96-well, 384-well, 1536-well plates, or even 9,600-microwell plates, for example. The present invention is not limited to the presently used microtiter plate configurations but provides for any configuration necessary to take advantage of today's industry standards as well as provides the flexibility to design for novel configurations.

The present invention provides a multiple level array system in which a substrate is patterned with a biomolecule, such as a protein or cell, using soft lithography techniques and elastomeric membranes. The multiple levels are achieved by either patterning multiple levels of biomolecules and/or utilizing multiple elastomeric membranes.

A first layer of an elastomeric membrane is used to pattern biomolecules onto a substrate. The membrane has through holes through which the biomolecules are patterned. A second membrane is placed on top of the first membrane, or alternatively, the first membrane is removed and the second is placed directly on the substrate. The second membrane has through holes that define reservoirs that encompass the microwells of the first membrane (or the patterned elements on the substrate).

The ability to pattern proteins in a multilevel array systems offers a vast improvement over the prior art method of assaying a particular protein by adding it to a standard microwell plate. When proteins are simply placed on a surface of a microwell plate, they adsorb non-specifically and denature and thus, loose their activity. The present invention overcomes this problem by arraying proteins on a substrate, preferably a SAM, which allows proteins to maintain their natural configuration and activity.

The present invention also provides for micro arrays of patterned cells in a particular spatial pattern to be later used in various cell based assays.

DETAILED DESCRIPTION OF THE INVENTION

Figure 1:
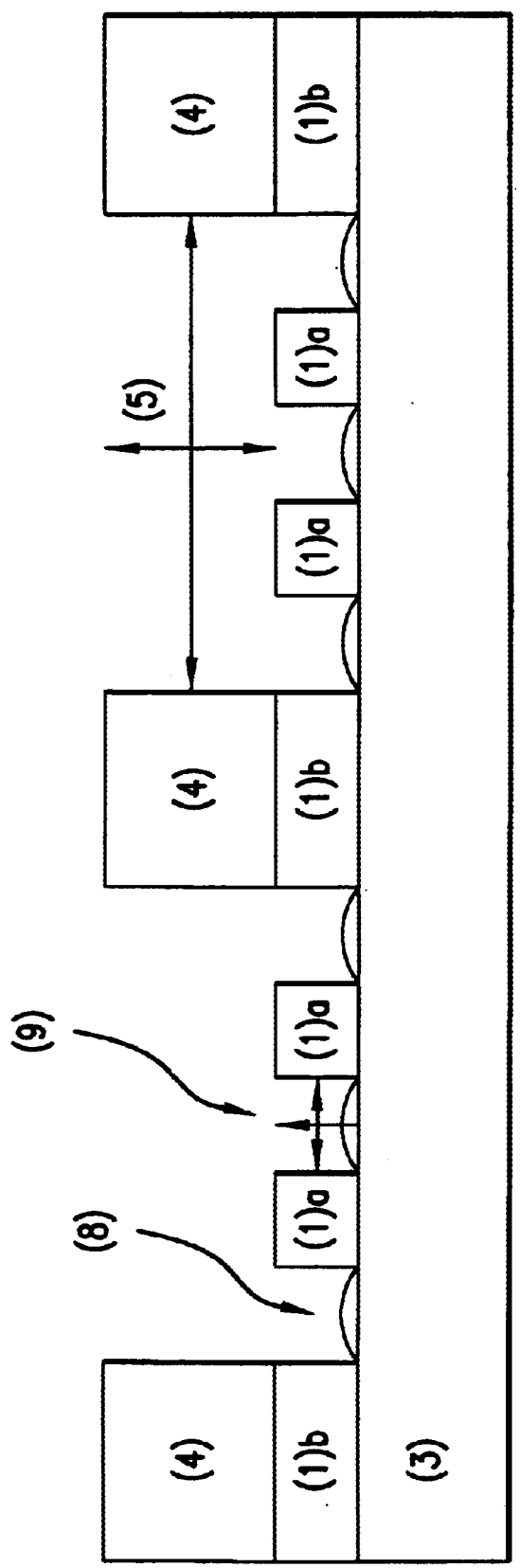
FIG. 1 is a schematic cross-sectional view of a multilevel array system. 1a in the figure depicts the membrane that defines the microwells. 1b in the figure depicts the membrane that defines the gaps between arrays.
Figure 2:
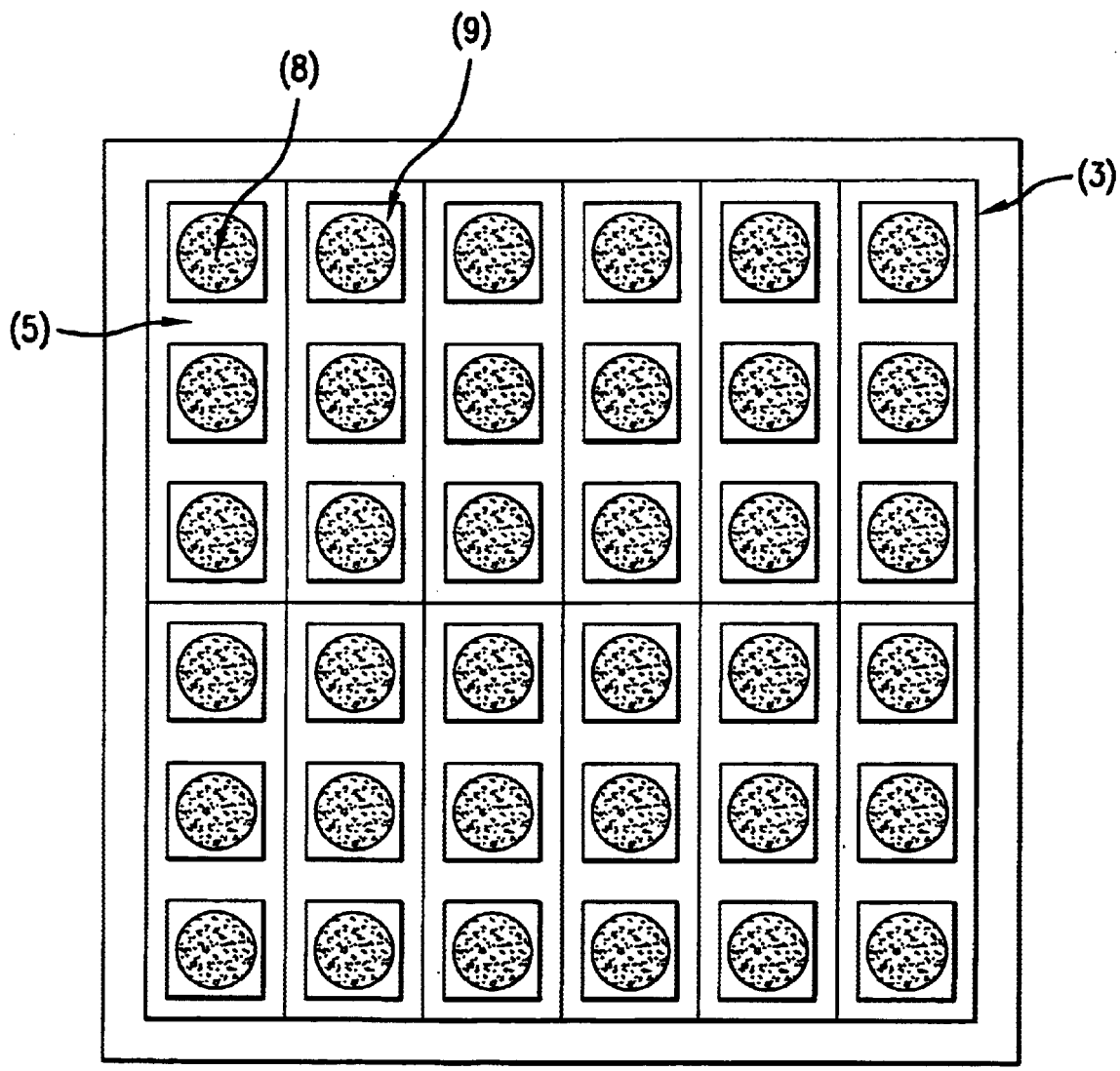
FIG. 2 is a schematic top-view illustration of a multilevel array system.

The present invention is directed to a multiple level array system. As shown in FIGS. 1 and 2, a bottom or substrate layer 3 is overlayed with a first layer 1 having through holes 9 that is used as a mask to allow patterning/deposition of biomolecules 8 onto the substrate layer 3. The biomolecules 8 may be of chemical, biochemical or biological origin. Mask layer 1 acts a stencil to allow deposition of biomolecules 8 onto substrate 3 in a patterned array defined by the configuration of the through holes 9 in the masking layer.

A suitable substrate 3 of the multiple level array system is essentially any material that can be used with a membrane including polymers, metals, ceramics, oxides, and the like. It is any surface on which an array is generated or with which an array is supported. Substrates may be of inorganic, organic, composite or polymeric origins. Typical materials are glass, silicon wafers, fused silica, metal films (gold, silver, copper, platinum, etc.) supported on any flat surfaces, polystyrene, poly(methylacrylate), and polycarbonate. The substrates may be further modified to support, accommodate, catalyze, or promote array generations, in which adsorption, chemical reaction, or physical interaction may occur between the modified surfaced and array elements.

Preferred substrate surfaces are those that are inert and/or capable of resisting the adsorption of biomolecules, such as proteins, by non-specific reactions. Non-specific adsorption is to be avoided as it would hamper the ability to immobilize specific biomolecules of interest and/or to immobilize biomolecules in specific locations. The surface of a substrate may be modified to exhibit specific interfacial characteristics, such as accommodating protein adsorption or resisting cellular attachment. According to a particularly preferred embodiment, a combination of gold as a substrate material and a molecular species having at least one sulfur-containing functional group such as a thiol, sulfide, or disulfide is selected. The interaction between gold and such sulfur-containing functional groups is a well-studied science, and a non-limiting representative exemplary list of such sulfur-containing functionalities may be found in an article entitled "Wet Chemical Approaches to the Characterization of Organic Surfaces: Self-Assembled Monolayers, Wetting and the Physical-Organic Chemistry of the Solid-Liquid Interface," by G. W. Whitesides and Paul E. Laibinis, Langmuir, 6, 87 (1990), incorporated herein by reference.

A substrate may also contain chemical or physical features on its surface. Physical features may correspond to surface indentations, projections, or combination of both. The chemical or physical features may be designed to conform to any desired format. For example, the substrate can have indentations that have a footprint corresponding to microwells of standard microtiter plates, such as a 6-well, 12-well, 24-well, 96-well, 384-well or 1,536-well microtiter plate or the like. "Footprint" means having a similar periodicity (the distance between) of features. For example, a substrate having indentations or projections with a 1,536-well microtiter plate footprint would have 1,536 indentations or projections spaced the same distance apart as the microwells of the 1536-well microtiter plate. Typically a 96-well plate has about a 1 cm distance between adjacent microwells; a 384-well plate has about 0.5 cm distance between adjacent wells; and a 1,536-well plate has about a 0.25 cm distance between adjacent wells.

The patterned biomolecules 8 are generated via conventional arraying techniques known in the art. Conventional techniques such as robotic arraying, silkscreen-printing, and ink-jet printing are used. Preferably, soft lithography is used. Soft lithography techniques are described in U.S. Pat. Nos. 5,512,131; 5,776,748; and 5976,826.

An advantage of using soft lithography techniques to create biomolecule arrays is that these techniques are compatible with biological materials. As these techniques do not involve the use of solvents or UV light, which are harmful to many biological materials they are uniquely suited for patterning proteins and cells. In addition, soft lithography techniques allow the fabrication and replication of patterns of biological materials in a very small scale, with feature sizes that range from about 1 $\mu$m to about 1 mm. Additionally, soft lithography techniques are lower in cost as the systems require little capital investment compared to conventional microfabrication techniques, and the materials themselves are low in cost. Further, soft lithography techniques allow patterning of SAMs, and the combination of biospecific ligands with thiols that resist non-specific adsorption.

Figure 3:
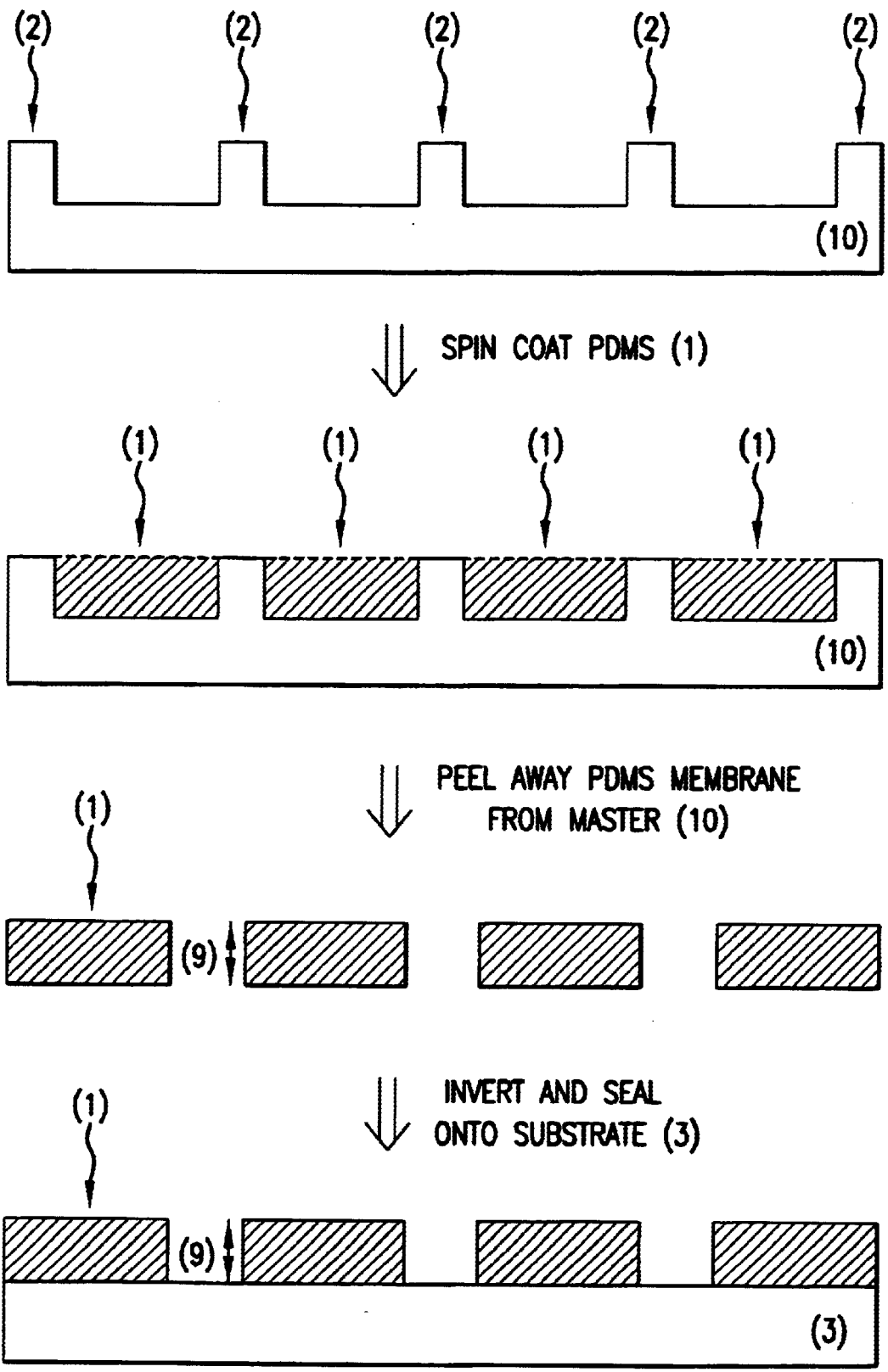
FIG. 3 depicts the formation of a PDMS membrane with through holes defined by projections present on a master.
Figure 4:
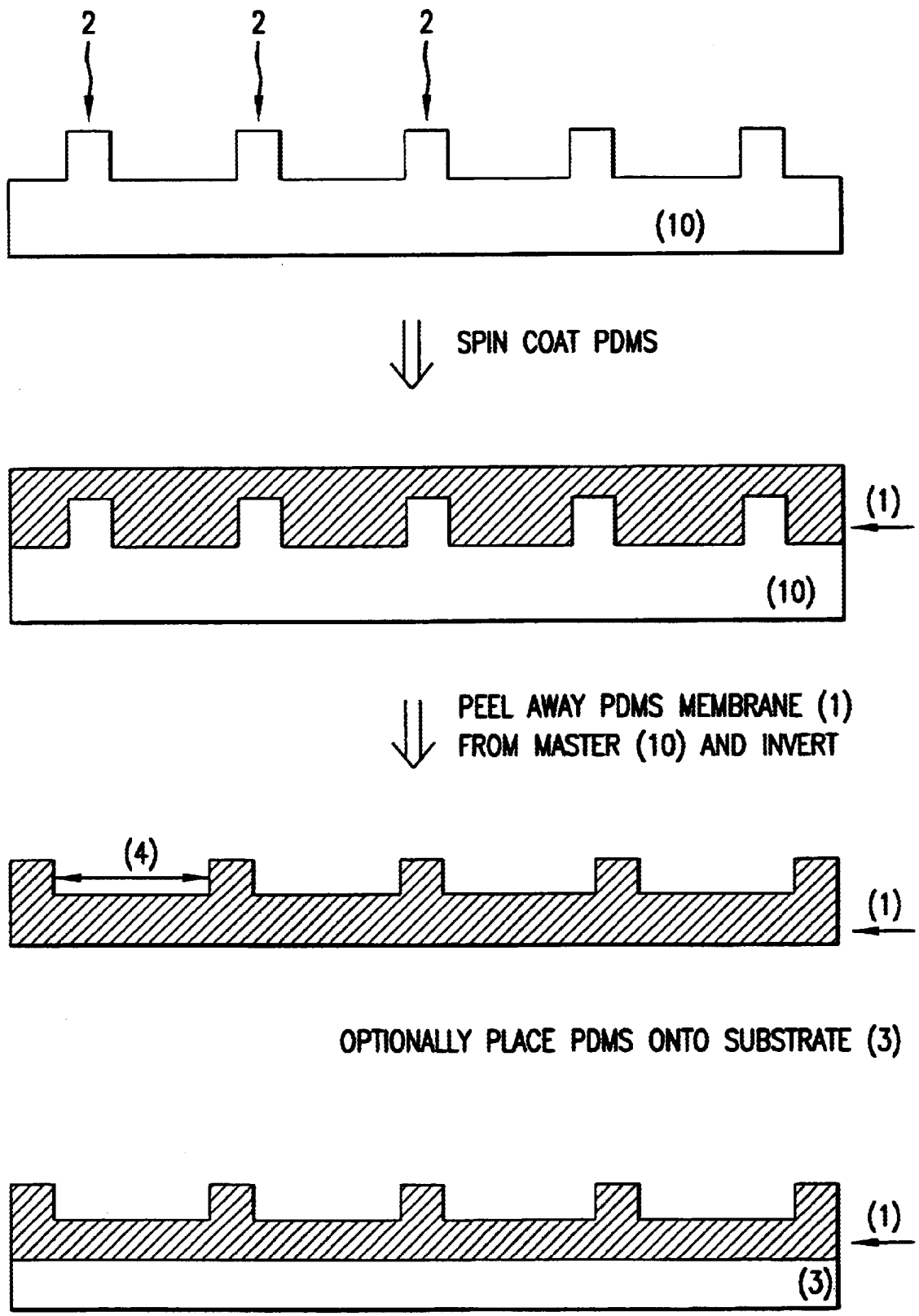
FIG. 4 depicts the formation of a PDMS membrane with microwells defined by the projections present on the master and optional placement on a substrate.
Figure 5A:
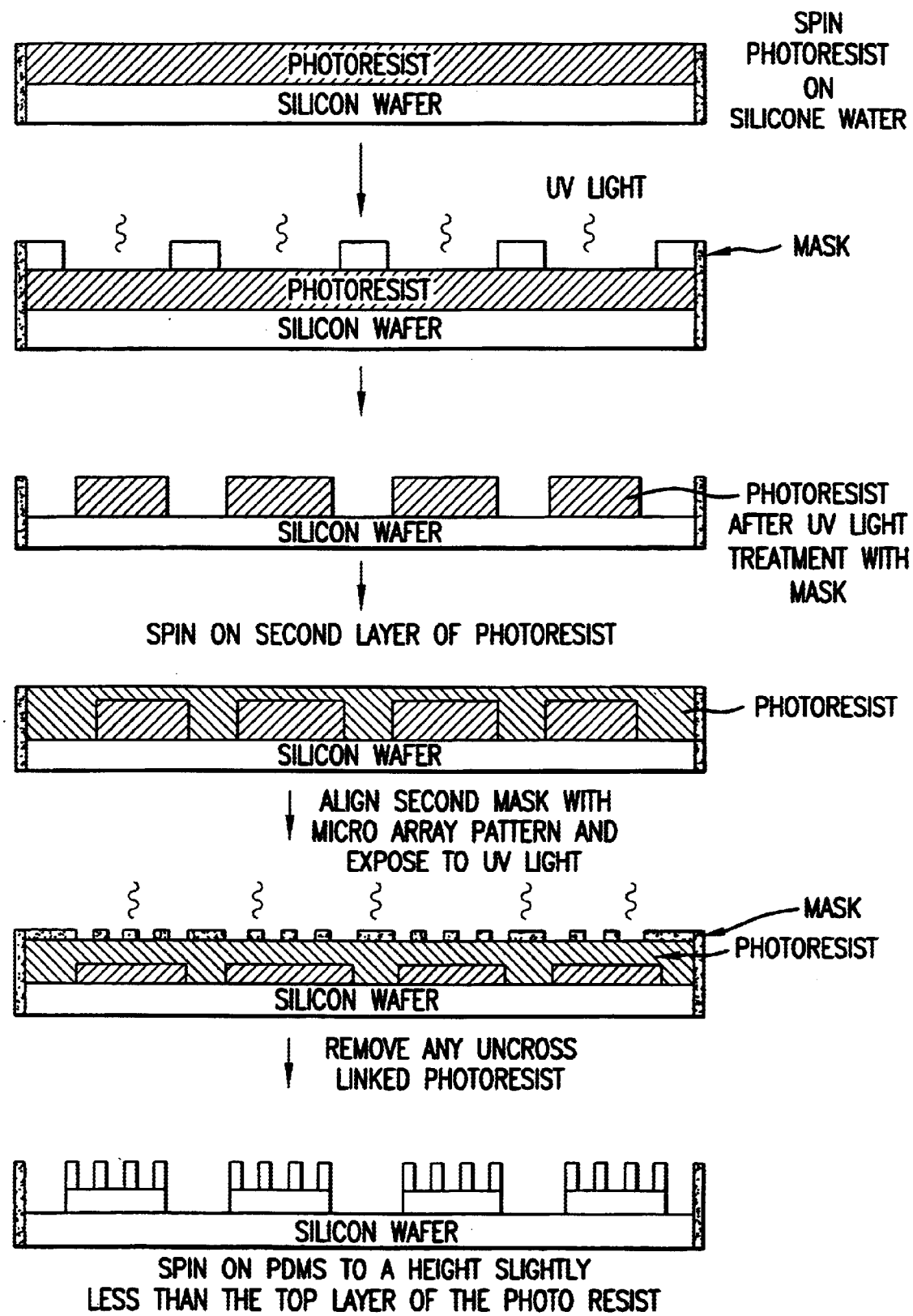
FIG. 5 is a schematic illustration of the formation of a multiple array in a single PDMS membrane system.
Figure 5B:
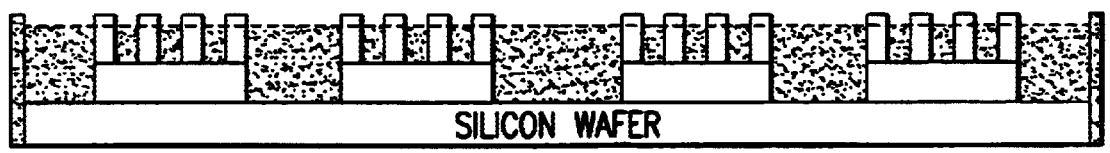
Figure 5B:
Figure 5B:
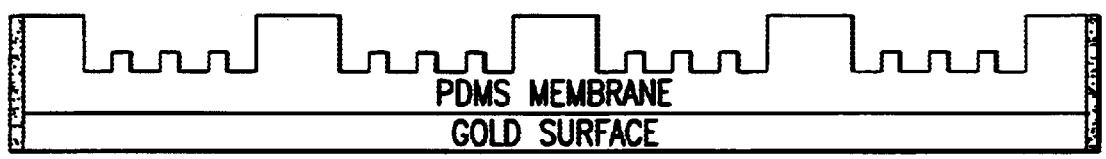

The common element in soft lithography techniques is a polymer template or membrane that contains features to be transferred or replicated. The pattern transfer element is produced by casting a liquid polymer precursor on a master, curing it to a solid, and removing it from the master. FIG. 3 depicts the formation of an elastomer membrane 1 having through holes 9. Through holes 9 are formed by projections 2 on a master 10. The liquid polymer is cast so that it comes to a level just slightly below the level of the projections so as not to cover the top surface of the projections on the master. The membrane 1 is peeled away from master 10 and placed on substrate 3. Biomolecules are then patterned onto substrate 3 using membrane 1 as a mask. FIG. 4 depicts the formation of an elastomer membrane 1 having microwells 4 instead of through holes. Microwells 4 are formed by a master having projections 2. The liquid polymer is cast so that it completely covers the top surface of the projections on the master. The membrane 1 is peeled away from the master 10 and is optionally placed on a substrate 3.

The mask layer 1, which is preferably an elastomeric membrane, is used as a mask for transferring materials that are deposited on a substrate. Additionally, the elastomeric membrane can be used as stamp to transfer chemical entities onto a substrate. When used as a stamp, the elastomeric membrane is fabricated to have projections. These projections will transfer chemical entities to a substrate by making contact with the substrate where the non-projected areas of the membrane will not contact the substrate and thus will not transfer chemical entities to these portions.

Preferably, membrane patterning is used to create a patterned surface. An arrayer, such as, but not limited to an ink-jet, is used to place biomolecules, such as proteins, cells, nucleic acids or chemical entities, onto a substrate. A membrane with through holes is used as a mask to produce a desired array/configuration of patterned biomolecules. Additionally, membrane patterning uses a membrane to mask those areas to be shielded from "activation." Membrane patterning facilitates shielding of a portion of a substrate surface from a reactant in solution, while exposing the rest of the surface (exposed by through holes in the membrane) to the reactant for chemical, biochemical, or biological reactions. These reactions are accomplished by the delivery of reagents via the through-holes in the membrane. These reactions may be activation reactions, conjugation, molecular recognition, covalent bond formation, ionic interactions, binding (i.e., ligand-substrate) events, catalytic reactions, hydrophobic interaction, affinity (i.e. antigen-antibody) interaction, hybridization, hydrogen-bond formation, etc.

In membrane patterning, the pattern-transfer element is any suitable material known in the art and is preferably formed of an elastomer as described by U.S. Pat. No. 5,512,131 by Kumar et al. entitled "Formation of Microstamped Patterns on Surfaces and Derivative Articles," incorporated herein by reference. Other exemplary elastomers are disclosed in U.S. Pat. No. 5,691,018 (Kelley et al.), incorporated herein by reference. A particularly preferred silicone elastomer is polydimethylsiloxane ("PDMS"). Exemplary PDMS membranes include those cast from prepolymer sold under the trademark Sylgard by the Dow Chemical Company, Midland Mich. Preferred Slygard prepolymers are Sylgard 182, Sylgard 184, and Sylgard 186.

A preferred casting method of the PDMS layer involves spin coating an elastomer on a master (See Duffy et al., Adv. Mater. 11, No. 7 (1999)). Another suitable casting method described by Kumar et al. (U.S. Pat. No. 5,512,131) involves pouring an elastomer precursor over a pattern. The height of the projections on the surface of the master set the maximum thickness of the membrane (typically 3–100 $\mu$m thick). After the PDMS membrane has cured, it is removed from the master.

As shown in FIGS. 1 and 2, a PDMS membrane 1 with the multiple through holes 9 is used as mask through which materials, such as biomolecules 8 or solutions containing biomolecules can be deposited onto a substrate 3. A PDMS membrane is sealed to a substrate to form a stencil or a mask. "Sealing" in this context is to be distinguished from the operation of other rigid or flexible masks that may be brought into contact with a surface, but that cannot seal to the surface. "Sealing" in this context means that when a membrane is contacted with a substrate surface and a fluid is applied to the masked surface, the fluid is allowed to contact only those portions of the masked surfaces in register with the through holes of the mask and the fluid does not pass under the mask and contact shielded portions of the substrate surface covered by solid portions of the mask. When a PDMS membrane and a substrate surface are brought in contact with each other, sealing occurs essentially instantaneously upon contact without application of significant pressure, and sealing can be maintained without any maintenance of pressure. The sealing is reversible, that is the membrane can be removed from the substrate surface by being peeled off, and can be reused on the same or a different substrate surface. A thicker membrane is sturdier and thus can be reused more often than a thinner membrane. In addition, the sealing can be made permanent by plasma oxidation of the membrane surface.

Any biomolecule, chemical entity or biochemical molecule can be arrayed in a pattern. Exemplary biomolecules are proteins, nucleic acids, and cells. Biomolecules may be immobilized on the surfaces of the previously described substrates by methods known in the art. Preferably, immobilization is performed using techniques that do not damage biological molecules. Exemplary methods known in the art include affinity capture, covalent derivatization, such as with 3-ethyl-1-[N,N-dimethyl-(3-aminopropyl)]-carbodiimide ("EDC")+N-hydroxysuccinimide ("NHS") direct coupling, and membrane anchoring, the use of streptavidin-biotin, nickel chelation capture and the like. Chemical species capable of activating the surface to react with another chemical or biochemical species may also be patterned on the surface. For example, self-assembled monolayers (SAMs) can be patterned onto a gold surface substrate. In addition to patterning biomolecules, the substrate may be patterned to contain both regions where the surface of the substrate and the array elements can interact and regions where they cannot. For example, micro-contact printing may be used to pattern SAMs, in which areas of hydrophobic and hydrophilic regions are generated.

SAMs are typically formed using molecules having functional groups that have a specific reactivity toward a particular surface. The remainder of the molecule is typically a hydrocarbon chain that interacts with neighboring molecules in the monolayer to form an ordered array. Monolayers with varying characteristics may be produced by having various functional groups at the terminal end of the SAM. For example, SAMs can be formed that are generally hydrophobic, hydrophilic, cytophobic, cytophilic, biophobic or biophilic. Such SAMs having specific binding affinities can be produced to allow production of patterned SAMs that adhere or repel cells, proteins, or other biological materials in specific and predetermined patterns. U.S. Pat. No. 5,976, 826 to Singhvi et al. is directed to derivatization and patterning of surfaces on SAMs and is incorporated herein by reference.

A preferred SAM is formed by alkanethiols [X—$CH_2$ ($CH_2$)$_n$SH], (hydrocarbons with a thiol or SH group at one end and a functional head group (represented by "X") at the terminal end) on a gold surface. "X" groups may be —$CH_3$, —OH, —CN, —C(O)$NH_2$, —$NH_2$, —$NO_2$, —$SO_3^-$, —$SO_2^-$, —O—$SO_3^{-2}$, —$PO_3^{2-}$, —$PO_3H^-$, —$PO_4^{3-}$ —$PO_3H_2$, —COOH, —$COO^-$, —($CF_2$)$_p$—$CF_3$ (where p=1–20) and 2-imidazole, as well as —COOR, —$NR_2$, —C(O)$NR_2$, where R is $C_1$–$C_4$. Further, the "X" groups need not be terminal provided they are accessible to interact with cells deposited on the surface. Thus, —C(O)NH—, —C(O)NHC(O)—, —C(S)NH—, —R—S—R, —R—S—S—R— and —R—O—R— groups are among the cytophilic functional groups that may be used. SAMS may also be used to render a surface cytophobic. A cytophilic or cytophobic material may be used to coat the SAM to make the surface more cytophilic or cytophobic. SAMs provide a base onto which other layers may be built and as such the nature of the surface may be modified as desired.

SAMs are created by the formation of metal-sulfur bonds between the surface and the thiol, and the subsequent crystalline close-packing of the hydrocarbon chains. By changing the X group, the SAM is engineered to have desired interfacial characteristics, i.e. wetting, adhesion, biocompatability, etc. For example, SAMs having the head group of $CF_3$ behave like a Teflon surface, while those having the head group of COOH show wetting characteristics of a glass surface. Thus, SAMs are able to render the surface resistant or susceptible to adsorption by polymers, proteins, or cells. Additionally, SAMs also allow for arraying of proteins that maintain their natural configuration and activity. Proteins placed directly on the surface of a microwell plate adsorb non-specifically, denature and loose their activity in contrast to proteins patterned onto SAMs.

Most preferably the surfaces are SAMs on gold substrates or gold coated surfaces of substrates. Preferred SAMs for cytophobicity are an alkanethiol terminated in oligo (ethylene glycol) ("OEG") groups as they provide a robust and well-characterized method for preventing non-specific adsorption of proteins to the gold. SAMs terminated with OEG groups are useful for their bio-inertness. The use of the OEG terminated SAMs reduces background noise as it repels non-specific binding of the "test" proteins and cells to the SAM.

The present invention is also directed to an embodiment in which a multiple level array system utilizes cells patterned onto a substrate. Multilevel array assay systems utilizing a patterned array of cells can provide a higher throughput in cell-based assays then currently available. For instances, the present invention provides for a high density array of cell patterning such that, in the area of a standard well of a 96-well plate (approximately 20 $mm^2$), over 2,000 array elements (such as cells, proteins, etc.) can be patterned.

Figure 6:
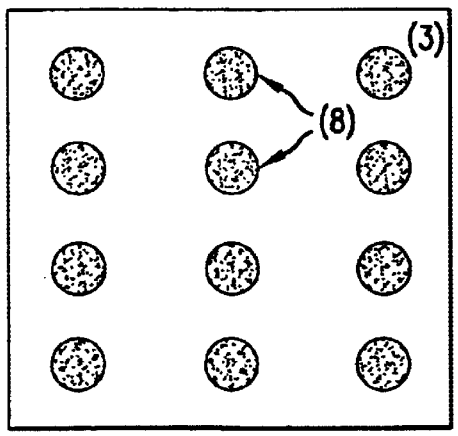
FIG. 6 is a schematic illustration of a patterned array. In this particular illustration 12 arrays of a biomolecule have been patterned onto a substrate.
Figure 7:
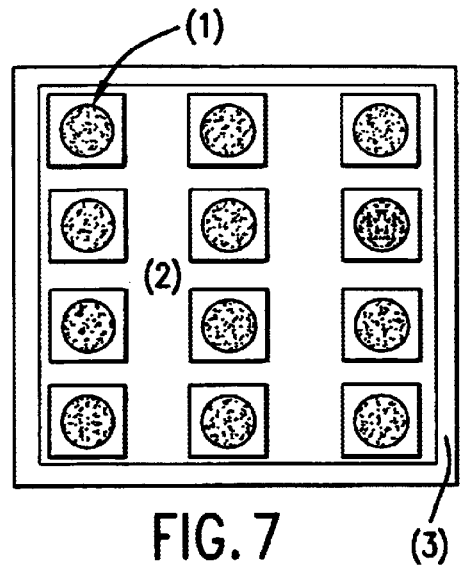
FIG. 7 is a schematic illustration of a membrane with through holes corresponding directly to the patterned arrays of immobilized biomolecules on the substrate below.
Figure 8:
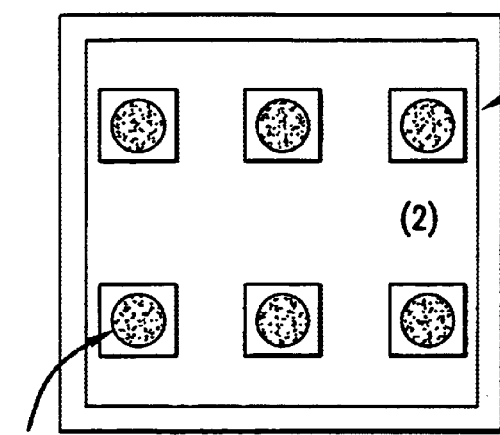
FIG. 8 is a schematic illustration depicting a membrane having through holes shielding a portion of the patterned array on the substrate below while exposing another portion of the array elements.
Figure 9:
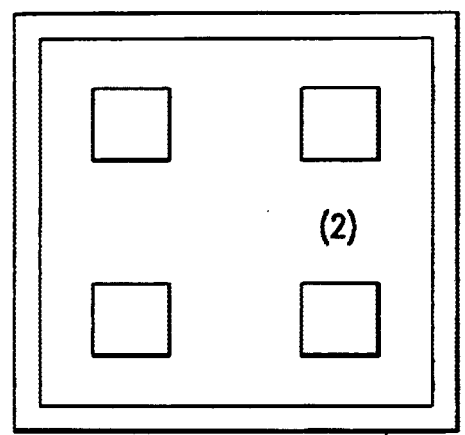
FIG. 9 is a schematic illustration depicting a membrane shielding all of the patterned arrayed elements below, but exposing portions of the substrate not have patterned elements.
Figure 10:
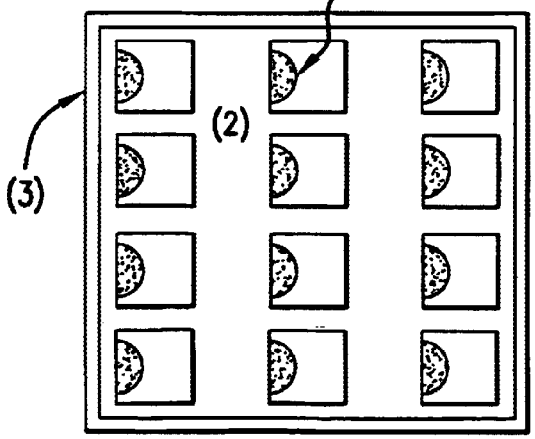
FIG. 10 is a schematic illustration depicting a membrane shielding half of each patterned array.

After an array of biomolecules 8 is generated (see FIG. 6, for example), an upper membrane 1 is placed on a substrate 3 (FIG. 7). The placement of a membrane is such that the through holes in the membrane directly register with array patterns (see FIG. 7); register with only certain elements in the array (see FIG. 8); or register with none of the patterned elements (see FIG. 9); or register with all or some of the elements of the array but only partially (e.g. registering only one half of each pattern)(see FIG. 10). Alternatively, instead of using a second (different) membrane after the arraying process, the membrane that was used as a mask to generate the array remains on the substrate. In this embodiment the through holes of the membrane mask obviously directly register with the array pattern. A second membrane with through holes defining reservoirs that encompass the through holes of the lower first membrane may be placed on top of the first membrane. If the membrane is left on after arraying, it is preferable to treat the membrane with a protein resistant surface treatment to reduce background "noise" due to non-specific protein binding.

A PDMS membrane is elastic and flexible so when it is placed on the surface of a substrate, it conforms to the contour of a substrate. Because the membrane seals against the substrate, fluid can be added later to the microwells 9 or reservoirs 5 (FIGS. 1 and 2), and such fluid will be contained within each microwell or reservoir in the membrane and will be hydraulically isolated from its adjacent openings. The term "microwell" means that the structure that forms on top of the patterned surface is composed of a bottom (defined by the top of the substrate) and sides (defined by sides of the through holes of the membrane). Alternatively, membranes may have "microwells" formed by the membrane itself, i.e. instead of having through holes the membrane has microwells formed by indentations in the membrane. See FIG. 4. This embodiment is useful when patterning of biomolecules directly on the membrane is desired and when patterning on a substrate is not necessary. The term "reservoir" is the through hole of an upper membrane layer. A reservoir diameter (when the openings are circular) or cross sectional area (when the openings are not circular such as oval, square, rectangular, and the like) can vary in size ranging from exactly matching the size of the microwell to having an opening that encompasses a plurality of microwells or even encompasses the entire array. Preferably the diameter or cross-sectional area of a reservoir will be larger than that of one microwell. More preferably a reservoir will have a diameter or cross sectional area that corresponds to the measurement of a microwell of a standard micro-titer plate, such as a 6-well, 12-well, 24-well, 96-well, 384-well, or 1536-well plate.

In a preferred embodiment, an upper membrane layer 4 (FIGS. 1 and 2) is sealed to the top surface of a lower membrane layer 1. Membrane 4 may be made from many different materials including organics, inorganics, polymers, and composites. A rigid material may be used to prepare membrane 4, but a preferred material is a polymer that has a characteristic of flexibility and elasticity. Most preferably membrane 4 is an elastomeric membrane such as PDMS. Where the multilevel array system will be used with conventional microtiter plate readers or arrayers a preferred membrane 4 is a rigid structure to allow for easily handling. Preferred rigid materials include polysytrene, polycarbonate, poly(methyl methacrylate), or glass.

The membrane 4 (FIGS. 1 and 2) contains at least one reservoir. The dimension of the reservoir 5 may vary to expose any number of the microwells 9. The periodicity of the openings (the distance between two adjacent openings) 6 may be as small as about 1 $\mu$m. If a multiple number of membranes are used, the size and periodicity of openings in each membrane may be the same or vary from each other. The thickness of a membrane can vary from about 1 $\mu$m to 1 cm. If the membrane if it is to be reused it is preferably greater than 50 $\mu$m thick.

FIGS. 1 and 2 depict membrane 4 containing multiple arrays of through holes, which define reservoirs 5 around the microarrays that were created by patterning biomolecules 8 through the through holes of the first membrane layer 1. FIG. 2 depicts a reservoir 5 encompassing three microwells. The reservoirs of the upper membrane can be of any size to encompass any desired number of microwells. Thus, for example, if it were desired to have the reservoirs match the size of microwells of a 6-well plate, the reservoirs would have a diameter of about 36 mm; reservoirs matching the size of the microwells of a 12-well plate would have a diameter of about 24 mm. In high density arrays using either a 96-well plate or a 1536-well plate configuration the reservoirs would be about 5 mm in diameter (96-well plate) or 1.7 mm in diameter (1536-well plate). Thus, it is clear that the microarrays of the present invention can be designed to accommodate any desired configuration or size of microwells and reservoirs. In one embodiment, the through holes or microwells of the first membrane are from about 1 $\mu$m to about 1 mm in diameter (cross sectional area from about 1 $\mu$m$^2$ to about 1 mm$^2$ and the reservoirs are from about 1.7 mm to about 5 mm in diameter (2.9 mm$^2$ to about 25 mm$^2$ cross sectional area). In another embodiment, the through holes of the first membrane are about 3 $\mu$m to about 500 $\mu$m in diameter (9 $\mu$m$^2$ to about 250,000 $\mu$m$^2$ cross sectional area).

Figure 11:
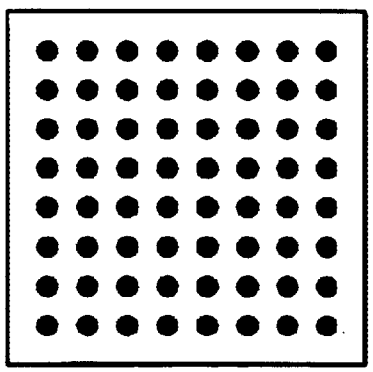
FIG. 11 depicts a PDMS membrane placed on top of a patterned substrate, exposing only a portion of the patterned elements. This allows a different assay to be performed in each reservoir defined by the through holes of the upper membrane.
Figure 11:
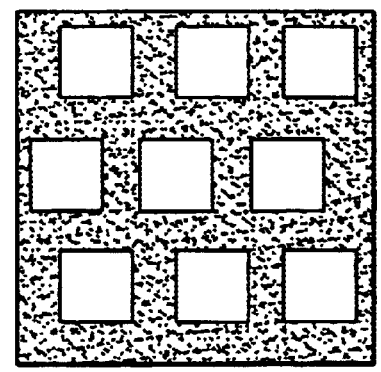
Figure 11:
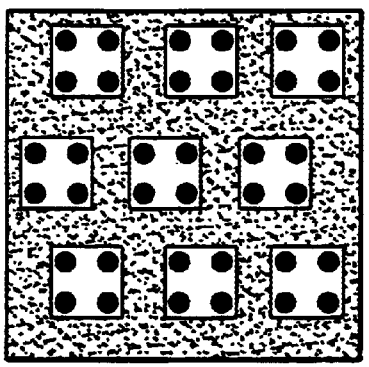
Figure 11:
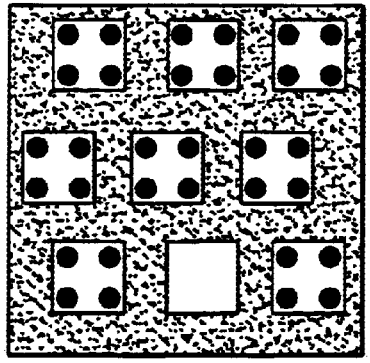

The configuration of through holes to produce the patterned array and the configuration of reservoirs are varied to include limitless array parameters. For example, FIG. 11 depicts the use of an uppermost PDMS membrane that has reservoirs encompassing only certain elements in the patterned array. In FIG. 11 the reservoirs encompass four patterned elements. This exemplary configuration allows one to perform a different reaction or assay in each reservoir. Additionally, the arrays may be of all the same biomolecule or all of the arrays may be of different biomolecule or any variation in between.

One embodiment of the invention is directed to a multiple level array system where the multiple levels of the array system are integrated in one elastomeric membrane. A preferred elastomeric membrane in this embodiment is PDMS. FIG. 5 illustrates the fabrication of a PDMS membrane having microwells 1 in the lower level of the membrane and having reservoirs 2 the upper level overlaying a plurality of microwells. Example 7 discusses the formation of an exemplary multilevel array membrane. A master is created having topological features corresponding to the desired through holes in the elastomeric membrane. The elastomer is spun onto the master and after curing, is peeled away. The membrane is then inverted and placed onto a suitable substrate. Preferred substrates are discussed above. The membrane will preferably have a configuration having microwells in the lower level of the membrane where the sides of the microwell are defined by the walls of the through holes of the membrane and the bottom of the microwell is defined by the top surface of the substrate. Preferably the through holes in the upper level of the membrane form reservoirs encompassing a plurality of microwells of the lower level. In a preferred embodiment, the upper reservoirs will have a footprint matching conventional microtiter plates such as a 6-well, 12-well, 24-well, 96-well, 384-well, or 1536-well microtiter plate. Alternatively, the microwells of the lower level are formed completely of the elastomer and thus, the bottoms, as well as the sides of the microwells, are defined by the elastomer. In this embodiment a microarray of biomolecules is patterned onto the substrate through the membrane or, in the case where the membrane has microwells instead of through holes in the lower level, biomolecules are patterned directly onto the bottom of the microwell formed by the elastomer. The preferred biomolecules are discussed above.

Figure 12:
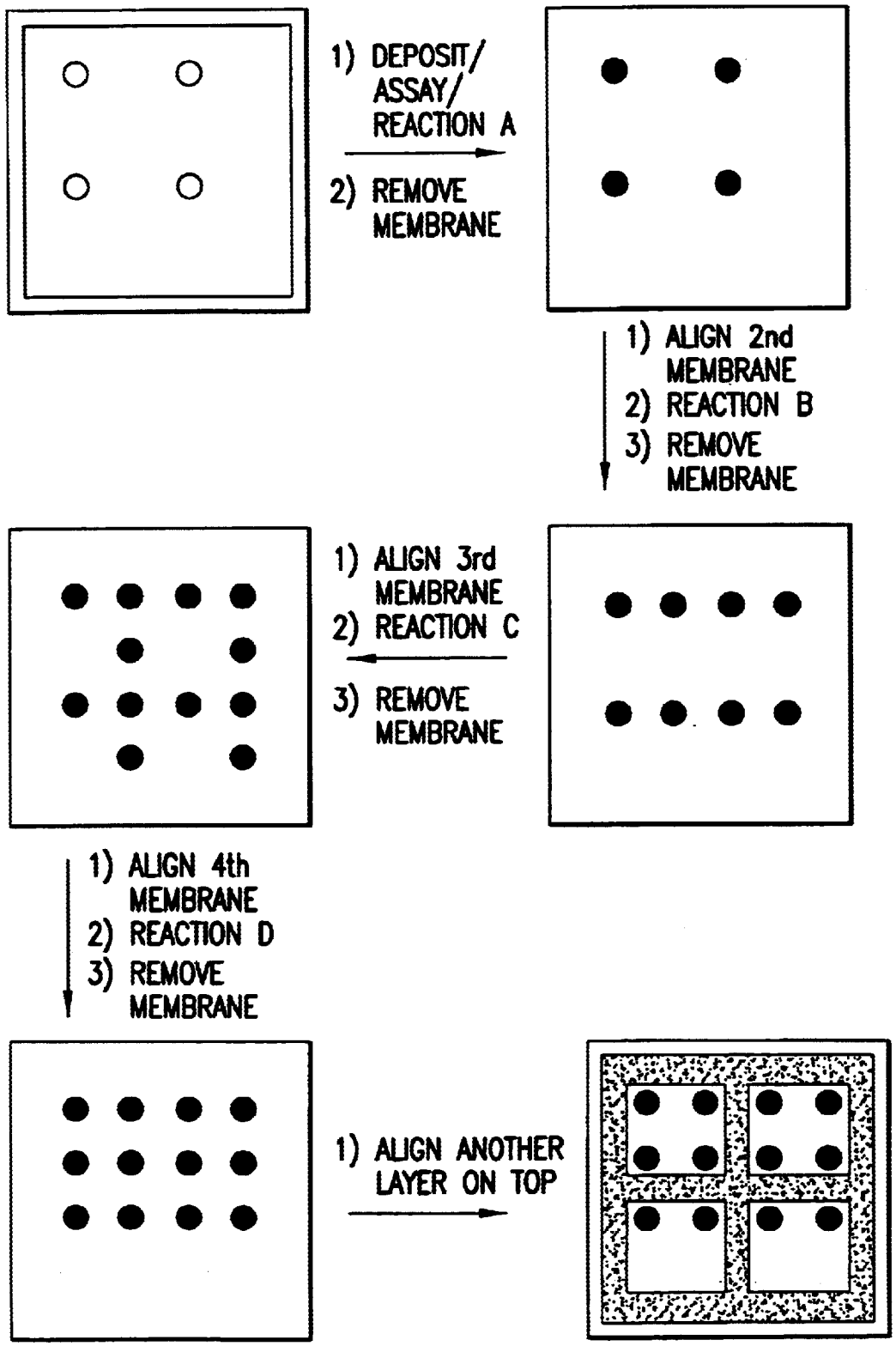
FIG. 12 depicts a multilevel array system utilizing multiple membranes to pattern an array on a substrate.

The present invention also provides for a successive use of multiple membranes having a different configuration of through holes. Instead of using a membrane with one through hole configuration, multiple membranes are used to generate multiple arrays. At each step of the process, a different array element may be patterned onto a substrate. After creating one array with one membrane, a second membrane is placed on top of the first array (including the first membrane) to expose only certain array elements, thereby creating an array within another array. FIG. 12 depicts an example of a successive use of multiple membranes. Generally, a first membrane is placed on top of a substrate. Using the first membrane as a stencil, material is deposited onto a substrate in the through holes. An assay is carried out or a reaction is allowed to proceed in each microwell. The membrane is removed. A second membrane is placed on top of the substrate. The size and periodicity of openings in this second membrane are such that a second deposition, assay, or reaction occurs directly on top, partially on top, or without overlapping the previously patterned elements. This membrane-alignment and material deposition process is repeated as many times as needed. When a final array has been generated, another membrane is placed on top of the array to either generate a collection of array elements that are assayed together or to isolate the patterned elements.

The number of configurations of multi levels array contemplated by this invention are limitless. In one embodiment the size, configuration, and periodicity of reservoirs in the upper membrane precisely match those of the patterned array on the substrate. For example, a first membrane that has 100 through holes is used as a mask to pattern 100 different proteins onto a substrate. A reaction is then performed in each of the 100 microwells formed by the through holes of the membrane and the top surface of the substrate. Another example of this embodiment occurs when, after patterning the 100 different proteins onto the substrate through the mask membrane, a second membrane having the exact footprint of the first membrane is placed on top of the first membrane to create a deeper microwell. Alternatively, the first membrane used for patterning may be removed and another membrane having the same footprint is placed onto the patterned substrate. Further, patterning of cells is performed onto a first membrane having microwells instead of through holes. A second membrane having through holes with the same footprint is placed on top of the first membrane.

Figure 13A:
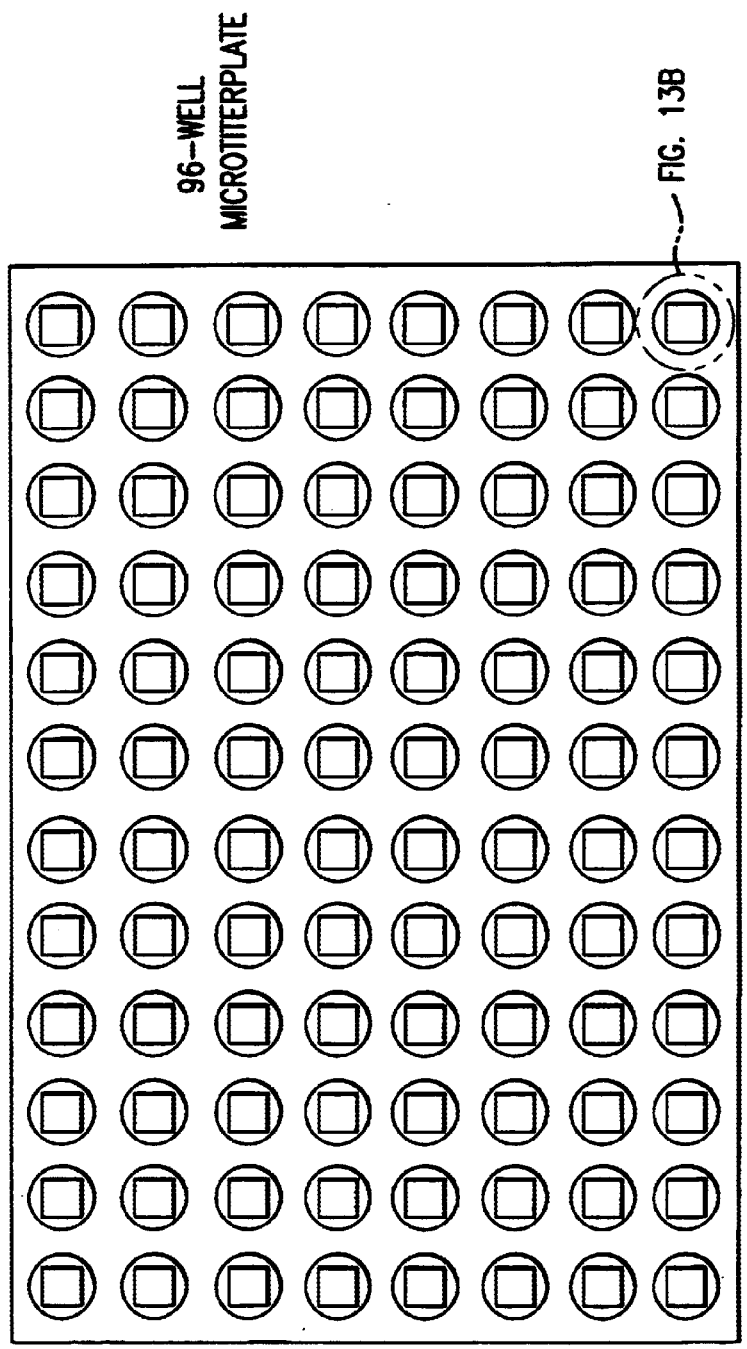
FIG. 13 depicts a multilevel array in which the reservoirs of the upper membrane have a 96-well plate footprint.
Figure 13B:
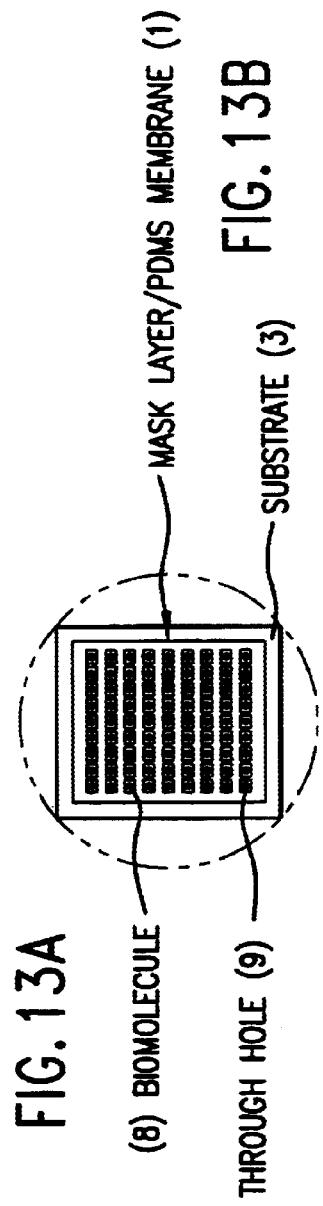

In another embodiment, the reservoirs in the upper membrane encompass a plurality of array elements to allow them to be assayed together. This embodiment is depicted in FIG. 12. Exemplary arrays include an upper membrane having a plurality of reservoirs that have a footprint (the size, configuration and periodicity of the through holes align with the wells) of a standard 6-well, 12-well, 24 well-, 96-well, 384-well, or 1536-well microtiter plate. FIG. 13 depicts a multilevel array system where the upper membrane has a 96-well footprint. For example a first membrane with 96×100 through holes is used to pattern 96 sets of 100 different biomolecules onto a substrate. A second membrane having 96 through holes is placed on top of the patterned substrate/first membrane combination. Each of the 96 through holes of the second membrane form a reservoir that encompasses one set of the 100 through holes of the first membrane. Thus, the 96 reservoirs of the second membrane each encompass 100 different through holes of the lower membrane, or in other words, each reservoir encompasses a set of 100 patterned proteins. A different reaction or assay is performed in each of the 96 reservoirs. This allows 100 different proteins to be assayed with 96 different reactions.

In a third embodiment, membranes having differing through holes are used to generate a multi-level array. FIG. 12 depicts an exemplary multiparameter array. The second, third, and fourth membranes in this figure all have a different through hole configuration.

Figure 14:
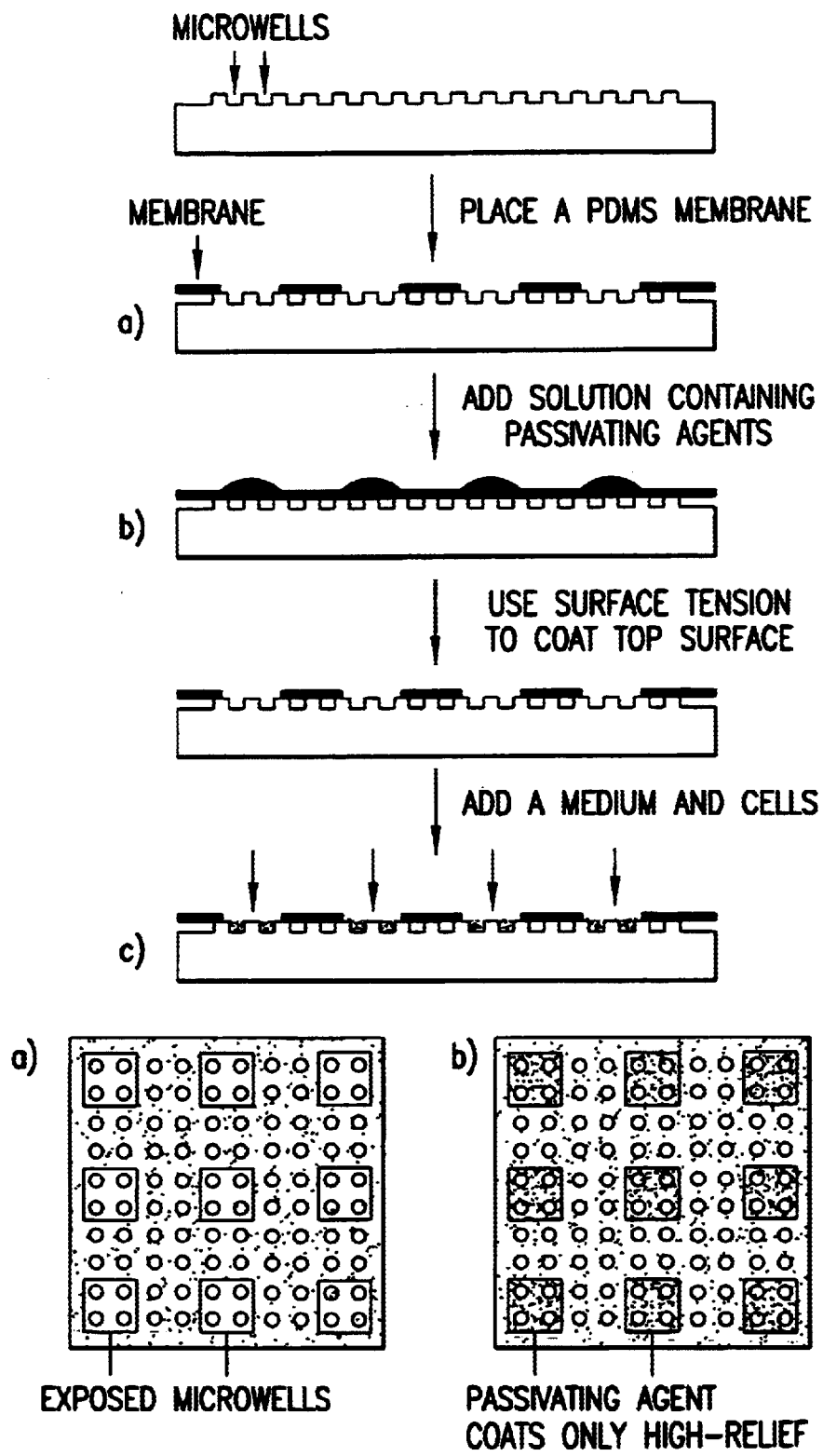
FIG. 14 depicts a multilevel array system employing a textured substrate and a membrane. A passivating agent is used to coat elevated areas in order to restrict cell attachment to these areas. This allows the deposition of cells into the microwells and allows the surrounding areas of the substrate to remain free from cells.

FIG. 14 depicts another embodiment of the present invention that combines a topologically patterned substrate and membrane(s). Although this embodiment can be used in many processes, it is particularly useful in cell biology. The topologically patterned substrate is caused by the substrate having either indentations or protrusions. Typically the indentations represent microwells on the surface of a substrate. The preferred microwells are capable of holding fluid volume of about 1 $\mu m^3$ (or 1 femtoL) to 1 ml.

In another preferred embodiment a first membrane with through holes is used to pattern 100 different biomolecules onto a substrate. A second membrane with through holes defining reservoirs encompassing the lower patterned biomolecules is placed on top of the first membrane. A reaction is carried out in each of the reservoirs. The entire multilevel array system is of a size small enough to allow placement into a microwell of a conventional microliter plate such as a 6-well, 12-well, 24-well, 96-well, 384-well or 1536-well plate. Further reactions then be performed in wells of the microtiter plates.

The projections or topological features on the substrate are prepared using methods known in the art. Substrates may be a polymeric replica, patterned photo resist on silicon or glass, or are preferably a PDMS pattern transfer element. Various soft lithographic techniques may be used to prepare a PDMS membrane or other replica to be used. Exemplary techniques include replica molding, micro-molding in capillaries, solvent-assisted micro-molding, and transfer molding. Replica molding, discussed above, involves casting a PDMS precursor against a master containing a surface relief that corresponds to the mirror image of the pattern to be generated. Micro-molding in capillaries involves placing a PDMS master against a substrate. Only the protrusions of the master contact the substrate, thus allowing a network of capillaries to form. These capillaries are filled with a polymeric precursor and are cross-linked to a solid. This results in the substrate having a structure that is a negative replica of the pattern on the PDMS. Solvent assisted molding involves generating a polymeric replica by imprinting the PDMS against a solvent-softened polymer. Transfer molding involves filling the relief-pattern of a PDMS mold with a liquid polymeric precursor and transferring to the surface of the substrate, which is later then cross-linked with a solid.

The preceding embodiments and the following examples represents just a few of the many possible arrays having multiple levels. These examples are not meant to limit the invention but are included to demonstrate methods of making a multitude of multiple level array combinations.

EXAMPLES

Example 1

Patterned Substrate and One PDMS Membrane

A gold film supported on silicon or glass is used with micro-contact printing ("μCP"). A PDMS stamp is inked with 1–3% (w/v) hexadecanethiol in ethanol. When the PDMS stamp is placed in contact with gold film, only the projections on the stamp contact the metal. Hexadecanethiol transfers from the stamp to the surface and forms SAMs of hexadecanethiolate. After removing the stamp, the gold film is washed with an ethanolic solution containing 1% HO(OCH$_2$CH$_2$O)$_6$(CH$_2$)$_{11}$SH. This thiol modifies the portion of the gold surface (making it cytophobic) where the μCP did not. The surface is washed with ethanol and dried under a gentle stream of nitrogen. The modified gold substrate is then immersed in a buffer solution (typically phosphate buffered saline) containing ~10 μ/ml of fibronectin (or another protein generally known as extracellular matrix proteins). The protein selectively adsorbs onto the hydrophobic regions (i.e. hexadecanethiol-modified surface); the protein does not adsorb on the oligoethylene glycol-modified surface. A membrane having a desirable size and periodicity of openings is placed on top of the patterned surface to generate an array of wells. A multiple array is thus created. The patterned proteins on the substrate provide a first array and a second array is formed by an upper membrane defining reservoirs around the patterned proteins.

A suspension of cells, such as for example, 3T3 and MDCK cells, may be added to each well. The cells pattern only on top of the protein-adsorbed areas. After cellular patterning, assays are carried out in each well.

After the bottom of each well has been patterned, the membrane may be removed to leave the patterned elements without damaging them, or the membrane may be left on the substrate and carry out assays by taking advantage of the formed microwells.

Example 2

Multilevel Array System Utilizing Patterned Cells

FIG. 14 depicts one embodiment of a multilevel array system that is useful in cell biology. A substrate, which can also be a PDMS membrane, has projections that form microwells. A PDMS membrane is placed on top this substrate. In FIG. 14 the upper membrane has through holes that define reservoirs encompassing a plurality of microwells, i.e. the through holes in the upper membrane are larger in diameter or have a wider opening defined by its cross sectional surface area. An aqueous solution containing a passivating agent such as serum albumin, β-casein, and hydrogels (such as lower molecular weight polyhydroxy ethyl methacrylate) in a concentration of 1 mg/ml of solvent is applied to this membrane-substrate structure. An aqueous solution does not wet the bottom of microwells, as the passivating agent coats only the top surface of the bottom membrane. Surface tension causes the passivating agents to coat only the upper structures. Thus, in this example, the passivating agent will only coat the upper PMDS membrane. Medium containing cells is then added to the structure. The cells will adsorb to all areas of the membrane/substrate complex that has not been coated with the passivating agent. Thus, in this figure, only the microwells of the substrate layer that were not masked with the uppermost PDMS membrane layers, will have cells absorbed.

Example 3

Patterning Proteins Onto SAMs Using the Multilevel Array System

A COOH terminated SAM substrate was formed as follows. The substrate was soaked in a 5:95 mixture of $HS(CH_2)_{10}$ $COOH:HS(CH_2)_{11}(CH_2O)_3OH$ ("OEG") at a total thiol 2 mM concentration in ethanol. A membrane having a footprint that matches a 96-well microtiter plate was placed over the substrate. Each well was filled with a buffer. Then the coupling agent 0.2 M EDC and 0.05 M NHS in water (pH 7.0) was added to the entire substrate/ microwell to activate the COOH-terminal groups. The reaction proceeded at room temperature for 20–30 minutes. Proteins were then added to each well. The proteins crosslink only to the SAMs terminated with carboxylic acids (the "activated" SAMs). The reaction proceeded at room temperature for 4 hours. Antibodies for proteins were used to confirm that attachment of the proteins to the bottom of the wells.

Example 4

An Exemplary Multilevel Microarray

A gold surface substrate is treated with a COOH terminated thiol to form a SAM. The SAM is then treated with EDC/NHS. A PDMS membrane containing 96×(10×10) of 100 μm diameter) through holes with each "micro-array" centered on a position corresponding to a well in a 96 well plate is sealed onto the SAM. The PDMS membrane is treated with inert materials (passivating agents) so that it resists the adsorption of proteins. Solutions of proteins (e.g. 100 different proteins from a library) are then transferred to the "exposed" COOH-terminated gold surface (defined by the 100 μm through holes in the membrane) using conventional arrayers such as an ink-jet. 100 different proteins are patterned within each array thus forming 96 identical microarrays of 100 different proteins on the footprint of a 96 well plate. A rigid piece of plastic containing an array of 96 through holes (5 mm in diameter), 9 mm apart, on a 8×12 array (8 rows of 12 through holes across the length), is then aligned and sealed to the 96 microarrays defined by the lower membrane. 96 separate assays on the 100 different proteins are then performed in each of the 5 mm wells. FIG. 13 depicts this configuration.

Example 5

An Exemplary Multilevel Array System Involving Removing the Membrane Used in Patterning The Example above is performed but after solutions of the 100 proteins are transferred to the exposed COOH-terminal gold surface, the first membrane is removed and replaced by an elastomeric membrane containing 8×12 (96) 5 mm diameter holes spaced by 9 mm. A rigid piece of plastic is then aligned and sealed to this membrane.

Example 6

Assay Using the Multilevel Array System 100 different kinase substrates (usually kinase proteins themselves) are patterned 96 times in a 10×10 array on a 96 well footprint. PDMS membranes are used to form a liquid-tight seal around each array of 100 kinases. 96 different solutions containing mixtures of kinases and 96 different drug candidates are added to 96 different wells containing the same 100 substrates. Phosphorylation of substrate, and hence effect of each drug on kinase-substrate interactions, is monitored by antibody detection. Effective drugs or "hits" are determined by inhibitor of phosphorylation.

Example 7

Fabricating Arrays of Arrays in One Elastomeric Membrane

As depicted in FIG. 16, a master is fabricated by spinning a layer of photo resist material onto a silicon wafer. A mask having a 96-well footprint is placed on the photo resist layer. This masked layer is exposed to UV light to produce a 96-well pattern on the first photo resist layer. A second layer of a photo resist material is spun onto the first layer. A mask having a pattern of through holes to create the desired microarray configuration is placed on top of the second photo resist layer and exposed to the UV light. Uncrosslinked photo resist is developed.

PDMS is spun onto the master at a height slightly lower than the second layer of the resist to form a PDMS membrane having a lower portion having through holes that correspond to the microarray pattern of the second layer of the photo resist. The PDMS membrane has an upper portion having reservoirs corresponding to the 96-well footprint of the first photo resist layer. Alternatively, to form microwells instead of through holes, the PDMS is spun onto the master to completely cover the photo resist master. The resulting PDMS membrane has microwells instead of through holes that correspond to the microarray pattern of the second layer of the photo resist. The PDMS membrane is then peeled away from the master and sealed to a suitable substrate such as gold.

Example 8

Microarray with a SAM with a Biospecific Ligand

Figure 15:
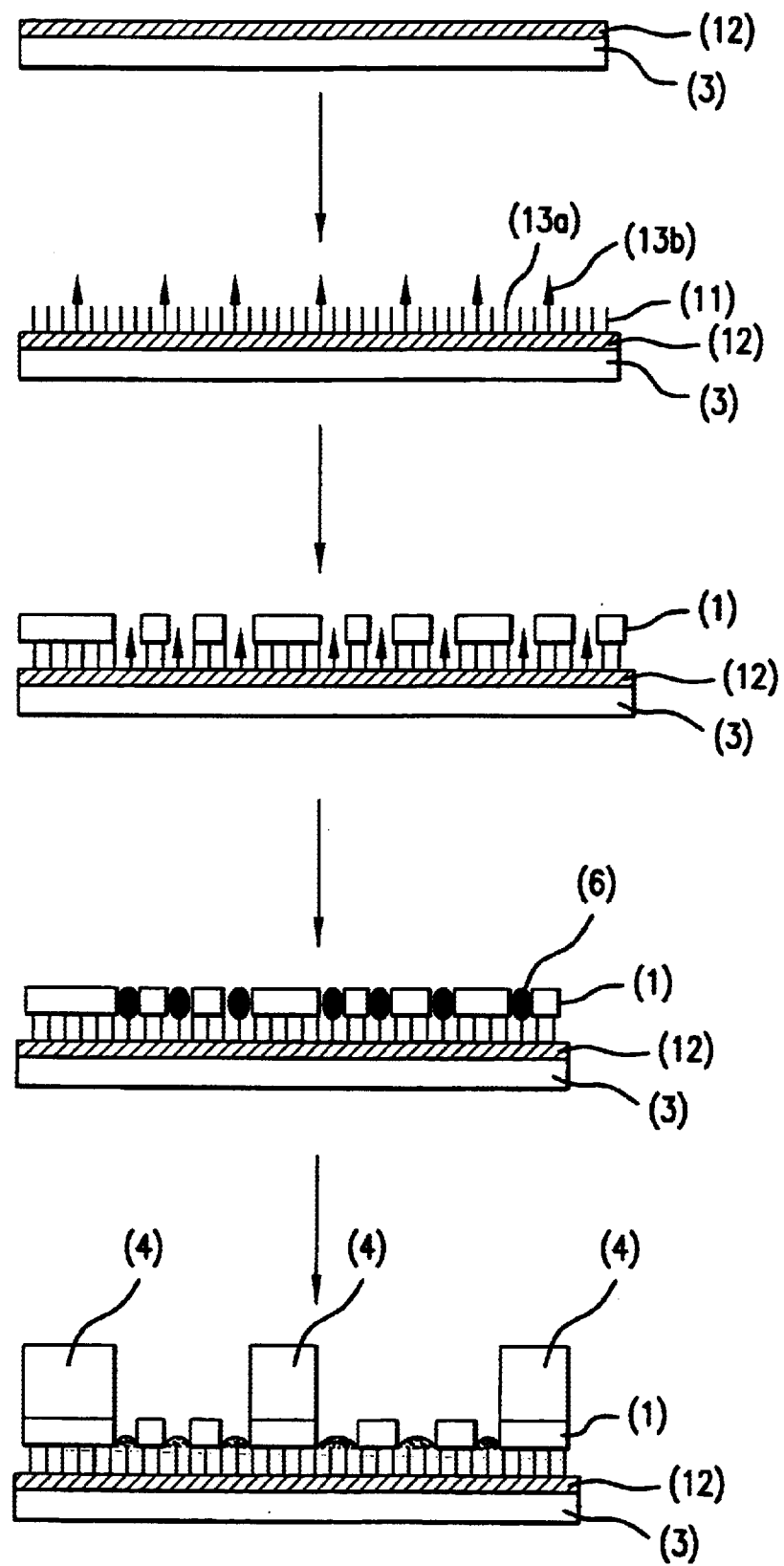
FIG. 15 depicts a micro array employing a SAM with biospecific ligands.

FIG. 15 depicts a microarray having an underlying substrate 3 such as glass or silicon. A metal coating 12, such as gold, silver, platinum, paladium or alloys is placed on top of the substrate 3. A SAM 11 is formed on top of the metal coating 12. The SAM 11 has a biospecific ligand 13a diluted with inert thiol 13b. Dilution of the ligand assists in reducing background noise caused by non-specific binding of a biomolecule to the SAM. An elastomeric membrane 1 is placed on top of the SAM. The membrane 1 has through holes, Proteins 6 are patterned onto the SAM through the through holes. A second membrane 4 is placed on top of the first membrane 1. The through holes of membrane 4 define reservoirs that encompass a plurality of the patterned proteins 6.

What is claimed is:

1. A multiple level microarray comprising a substrate, and a lower membrane having through holes, wherein the lower membrane seals to the substrate, and further providing an upper membrane overlaying the lower membrane, the upper membrane having at least one through hole defining a reservoir, and wherein the through holes of the lower membrane have a 96-well, 384-well or 1536-well microtiter plate footprint.

2. The micro-array of claim 1 wherein the reservoir(s) of the upper membrane encompasses a plurality of through holes of the lower membrane.

3. The micro-array of claim 1 wherein the reservoirs of the upper membrane have a 6-well, 12-well, 24-well, 96-well, 384-well or 1536-well microtiter plate footprint.

4. The micro-array of claim 1 further comprising a substrate having a patterned array of biomolecules.

5. The micro-array of claim 4 wherein the biomolecules are selected from the group consisting of cells, proteins, and nucleic acids.

6. The micro-array of claim 1 wherein the through holes in the lower membrane have a diameter from about 1 $\mu$m to 1 mm.

7. The micro-array of claim 1 wherein the through holes in the lower membrane have a cross-sectional area from about 1 $\mu m^2$ to 1 m $m^2$.

8. The micro-array of claim 1 wherein the through holes in the lower membrane have a diameter from about 3 $\mu$m to about 500 $\mu$m.

9. The micro-array of claim 1 wherein the through holes in the lower membrane have a cross sectional area from about 9 $\mu m^2$ to about 250,000 $\mu m^2$.

10. The micro-array of claim 1 wherein the reservoirs of the upper membrane have a diameter from about 0.5 mm to about 36 mm.

11. The micro-array of claim 1 wherein the reservoirs of the upper membrane have a diameter from about 1.7 mm to about 5 mm.

12. The micro-array of claim 1 wherein the reservoirs of the upper membrane have a cross-sectional area from about 0.25 $mm^2$ to 1296 $mm^2$.

13. The micro-array of claim 1 wherein the lower membrane layer is formed of an elastomeric material.

14. The micro-array of claim 13 wherein the elastomeric material is PDMS.

15. The micro-array of claim 1 wherein the upper membrane layer is formed of PDMS.

16. The micro-array of claim 1 further comprising a SAM, wherein the SAM is formed on top of the substrate.

17. The micro-array of claim 16 wherein the SAM is formed of an alkanethiol.

18. A multiple level micro-array comprising a substrate having at least one patterned microarray and an upper membrane formed of an elastomeric material overlaying the at least one patterned microarray, wherein the upper membrane comprises at least one reservoir encompassing at least one patterned microarray on the substrate, and wherein the at least one patterned microarray corresponds to a 96-well 384-well or 1536-well microtiter plate footprint.

19. The micro-array of claim 18 wherein the patterned array comprises biomolecules.

20. The micro-array of claim 19 wherein the biomolecules are selected from the group consisting of cells, proteins, and nucleic acids.

21. The micro-array of claim 18 wherein the at least one reservoir of the upper membrane has a diameter from about 0.5 mm to about 36 mm.

22. The micro-array of claim 18 wherein the at least one reservoir of the upper membrane has a diameter from about 1.7 mm to about 5 mm.

23. The micro-array of claim 18 wherein the at least one reservoir of the upper membrane has a cross-sectional area from about 0.25 $mm^2$ to 1296 $mm^2$.

24. The micro-array of claim 18 wherein the elastomeric material is PDMS.

25. The micro-array of claim 18 further comprising a SAM, wherein the SAM is formed on the substrate.

26. The micro-array of claims 25 wherein the SAM is formed of an alkanethiol.

27. A method of forming a multilevel micro-array comprising patterning biomolecules onto a substrate through a first membrane having through holes that define a pattern, and further comprising overlaying a second membrane on top of the first membrane, wherein the second membrane has a plurality of through holes defining reservoirs encompassing the patterned biomolecules, and wherein the biomolecules are patterned in a 96-well, 384-well or 1536-well microtiter plate footprint.

28. A multilevel micro-array system comprising a substrate and an elastomeric membrane overlaying a substrate, wherein the membrane has a lower level and an upper level, wherein the lower level has a plurality of through holes that form microwells, wherein the microwells are defined by the sides of the through holes of the lower level of the membrane and the bottom of the microwells are defined by the top surface of the substrate, and wherein the upper level of the membrane has through holes forming reservoirs that encompass a plurality of microwells of the lower level, and wherein the through holes of the lower membrane have a 96-well, 384-well or 1536-well microtiter plate footprint.

29. The micro-array of claim 28 wherein the reservoir(s) of the upper membrane encompasses a plurality of through holes of the lower membrane.

30. The micro-array of claim 28 wherein the reservoirs of the upper membrane have a 6-well, 12-well, 24-well, 96-well, 384-well or 1536-well microtiter plate footprint.

31. The micro-array of claim 28 further comprising a substrate having a patterned array of biomolecules.

32. The micro-array of claim 31 wherein the biomolecules are selected from the group consisting of cells, proteins, and nucleic acids.

33. The micro-array of claim 28 wherein the through holes in the lower membrane have a diameter from about 1 $\mu$m to 1 mm.

34. The micro-array of claim 28 wherein the through holes in the lower membrane have a cross-sectional area from about 1 $\mu m^2$ to 1 $mm^2$.

35. The micro-array of claim 28 wherein the through holes in the lower membrane have a diameter from about 3 $\mu$m to about 500 $\mu$m.

36. The micro-array of claim 28 wherein the through holes in the lower membrane have a cross-sectional area, from about 9 $\mu m^2$ to about 250,000 $\mu m_2$.

37. The micro-array of claim 28 wherein the reservoirs of the upper membrane have a diameter from about 0.5 mm to about 36 mm.

38. The micro-array of claim 28 wherein the reservoirs of the upper membrane have a diameter from about 1.7 mm to about 5 mm.

39. The micro-array of claim 28 wherein the reservoirs of the upper membrane have a cross-sectional area from about 0.25 $mm^2$ to 1296 $mm^2$.

40. The micro-array of claim 28 wherein the lower membrane layer is formed of an elastomeric material.

41. The micro-array of claim 40 wherein the elastomeric material is PDMS.

42. The micro-array of claim 28 wherein the upper membrane layer is formed of PDMS.

43. The micro-array of claim 28 further comprising a SAM, wherein the SAM is formed on top of the substrate.

44. The micro-array of claim 43 wherein the SAM is formed of an alkanethiol.

45. A multilevel micro-array system comprising an elastomeric membrane having a lower and an upper level, wherein the lower level of the membrane has microwells, and wherein the upper level of the membrane has through holes forming reservoirs that encompass a plurality of microwells of the lower portion, and wherein the microwells have a 96-well, 384-well or 1536-well microtiter plate footprint.

* * * * *